US007553822B2

(12) United States Patent
Kaye et al.

(10) Patent No.: US 7,553,822 B2
(45) Date of Patent: Jun. 30, 2009

(54) COMPOSITIONS AND METHODS FOR INHIBITING TRANSLATION OF A MECT1-MAML2 CHIMERIC GENE

(75) Inventors: Frederic J. Kaye, Potomac, MD (US); Takefumi Komiya, Osaka (JP)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/698,070

(22) Filed: Oct. 30, 2003

(65) Prior Publication Data

US 2005/0095709 A1     May 5, 2005

(51) Int. Cl.
*A61K 31/70*   (2006.01)
*C07H 21/40*   (2006.01)
*C12N 15/00*   (2006.01)

(52) U.S. Cl. ................ 514/44; 536/23.1; 536/24.5; 435/320.1

(58) Field of Classification Search ................ None
See application file for complete search history.

(56) References Cited

U.S. PATENT DOCUMENTS

| 6,331,425 | B1 * | 12/2001 | Taylor et al. ................ 435/200 |
| 6,506,559 | B1 | 1/2003 | Fire et al. |
| 6,573,099 | B2 * | 6/2003 | Graham ................ 435/455 |
| 2004/0006005 | A1 * | 1/2004 | Bhanot ................ 514/8 |
| 2004/0086884 | A1 * | 5/2004 | Beach et al. ................ 435/6 |

FOREIGN PATENT DOCUMENTS

WO     WO 03/004645 A1     1/2003

OTHER PUBLICATIONS

Wilda et al. Oncogene 2002, vol. 21, pp. 5716-5724.*
Tonon et al. Nature Genetics 2003 vol. 33, pp. 208-213.*
Sui et al. PNAS 2002, vol. 99, pp. 5515-5520.*
Nicklin et al. Current Gene Therapy 2002, vol. 2, pp. 273-293.*
Elbashir et al. EMBO Journal 2001, vol. 20, pp. 6877-6888.*
Parrish et al. Molecular Cell 2000, vol. 6, pp. 1077-1087.*
Amarzguioui et al. Nucleic Acids Research 2003, vol. 31, pp. 589-595.*
Saxena et al. Journal of Biological Chemistry 2003, vol. 45, pp. 44312-44319.*
Wu et al. Molecular and Cellular Biology 2002, vol 22, pp. 7688-7700.*
Bass Nature 2001, vol. 411, pp. 428-429.*
Opalinska et al. Nature Reviews Drug Discovery, 2002, vol. 1, p. 503-514.*
Tonon et al., "t(11;19)(q21;p13) translocation in mucoepidermoid carcinoma creates a novel fusion product that disrupts a Notch signaling pathway," *Nature Genetics*, 33, 208-213 (Feb. 2003).
Iourgenko et al., "Identification of a family of cAMP response element-binding protein Coactivators by genome-scale functional analysis in mammalian cells," *PNAS Early Edition*, 1-6 (2003).
Conkright et al., "TORCs: Transducers of Regulated CREB Activity," *Molecular Cell*, 12, 413-423 (Aug. 2003).
Wilda et al., "Killing of leukemic cells with a *BCR/ABL* fusion gene by RNA interference (RNAi)," *Oncogene*, 21, 5716-5724 (2002).
Sui et al., "A DNA vector-based RNAi technology to suppress gene expression in mammalian cells," *PNAS*, 99 (8), 5515-5520 (Apr. 2002).
Shi, "Mammalian RNAi for the masses," *Trends in Genetics*, 19 (1), 9-13 (Jan. 2003).
Aoki et al., "RNA Interference may be More Potent Than Antisense RNA in Human Cancer Cell Lines," *Clinical and Experimental Pharmacology and Physiology*, 30, 96-102 (2003).
Cioca et al., "RNA interference is a functional pathway with therapeutic potential in human myeloid leukemia cell lines," *Cancer Gene Therapy*, 10, 125-133 (2003).
Brummelkamp et al., "Stable suppression of Tumorigenicity by virus-mediated RNA interference," *Cancer Cell*, 2, 243-247 (Sep. 2002).
Lin et al., "D-RNAi (Messenger RNA-antisense DNA Interference) as a Novel Defense System Against Cancer and Viral Infections," *Current Cancer Drug Targets*, 1, 241-247 (2001).
Borkhardt, "Blocking oncogenes in malignant cells by RNA interference-New hope for a highly specific cancer treatment?," *Cancer Cell*, 167-168 (Sep. 2002).
Jang et al., "Suppression of adenine nucleotide translocase-2 by vector-based siRNA in human breast cancer cells induces apoptosis and inhibits tumor growth in vitro and in vivo," *Breast Cancer Research*, 10(1): 1-14 (Epub Feb. 12, 2008).
Kong et al., "Respiratory syncytial virus infection in Fischer 344 rats is attenuated by short interfering RNA against the RSV-NS1 gene," *Genetic Vaccines and Therapy*, 5 (4), 1-8 (Epub Feb. 1, 2007).

* cited by examiner

*Primary Examiner*—Tracy Vivlemore
(74) *Attorney, Agent, or Firm*—Leydig, Voit & Mayer, Ltd.

(57) ABSTRACT

Composition for the inhibition of the translation of a Mect1-MAML2 chimeric gene consisting essentially of: (a) a fragment of the nucleic acid encoding the chimeric gene, and (b) a nucleic acid complementary to the fragment, and a method of inhibiting the translation of a Mect1-MAML2 chimeric gene comprising contacting a cell expressing the chimeric gene with the composition, whereupon the translation of the chimeric gene is inhibited.

31 Claims, 2 Drawing Sheets

SEQ ID NO: 1 aggtggcggc gagaagatgg cgacttcgaa caatccgcgg aaattcagcg agaagatcgc gctgcacaat cagaagcagg
cggaggagac ggcggccttc gaggaggtca tgaaggacct gagcctgacg cgggccgcgc ggctccaggg ttccttgaaa
agaaaacagg tagttaacct atctcctgcc aacagcaagc gacccaatgg ctttgtggac aactcatttc ttgatatcaa
aagaattcgt gttggggaga atctctctgc aggacaaggt ggcctccaaa taaacaatgg acaaagtcag attatgtcag
ggaccttgcc tatgagccaa gcaccectgc gaaagactaa cactctgcca tcccatacac attctcctgg caatggcctg
tttaacatgg gcttaaagga ggtaaagaag gagccaggag agactctgtc ttgcagtaag cacatggatg gccaaatgac
ccaagagaat attttccta ataggtacgg agacgaccct ggagaacaac tgatggatcc tgagctgcag gaactgttca
atgaactgac caacatatct gtgcctccca tgagtgacct tgaactggag aacatgatca atgccaccat aaagcaggat
gacccattta acattgactt gggtcagcaa agccagagga gcacacctag gccctcctta cccatggaga aaatagtgat
caaaagtgaa tactcaccgg gcttgactca gggcccctca ggctctcctc agctgaggcc cccatcagct ggccccgcat
tctccatggc caactctgcc ctctccactt cgtctccaat cccttcagtc cctcagagcc aggctcagcc tcagacaggc
tccggagcaa gccgggcctt gccaagctgg caggaagtat cccatgccca gcagctcaaa cagatagctg ctaatcgtca
gcagcatgcc cggatgcagc agcaccagca gcagcaccag cctaccaact ggtcagcctt gccctcctct gctggaccat
caccaggtcc atttgggcag gagaaaatcc ccagcccttc tttggtcag cagacattca gcccacagag ctcccccatg
cctggggtag ctggcggcag cggccagtcg aaagtaatgg ctaactacat gtacaaggcc ggccctcag cccagggtgg
gcacctagat gtcctcatgc agcaaaagcc tcaggatctc agtcgaagtt ttattaacaa cccgcaccca gccatggagc
cccgtcaggg caacaccaag cctttgtttc attttaactc agatcaagcg aaccagcaga tgccttctgt tttgccttcc
cagaacaagc cttctctcct acactacacc caacagcaac agcagcaaca gcagcagcag cagcagcagc agcagcagca
acagcagcag cagcagcaac agcaacagca acagcaacag cagagttcaa tttcagctca acaacagcaa cagcagcaga
gctcaatttc agcccaacag cagcagcagc agcaacaaca gcagcagcag cagcaacaac aacagcaaca acagcagcag
cagcagcagc aacaaccatc ttctcagcct gcccaatctc taccaagcca gcctttgcta aggtcacctt tgccacttca
gcaaaagctc ctacttcagc aaatgcagaa tcagcccatt gcaggaatgg gataccaagt ctcccaacaa cagagacagg
atcaacactc tgtggtaggc cagaacacag gccccagtcc aagtcctaac ccctgctcaa atccaaacac tggaagtggt
tacatgaact cccagcaatc actgttgaat cagcaattga tgggaaagaa gcagactcta cagaggcaga tcatggagca
gaaacagcaa cttcttctcc agcagcagat gctggctgac gcggagaaaa ttgctccaca agatcagata aaccgacatt
tgtcaaggcc acctccagat tataaagacc aaagaagaaa tgtgggcaat atgcaaccaa ctgctcagta ttctggtggc
tcatccacaa taagcttaaa ctctaaccag gctttggcaa acccagtttc aacacacacc attttaactc ccaattccag cctcctgtct
acttctcacg ggacaagaat gccatcatta tctacagcag ttcagaatat ggggatgtat ggaaatctgc cttgtaatca
acctaacaca tacagtgtca cttcaggaat gaatcaattg acccaacaga gaaacccaaa gcaattgtta gcaaatcaaa
acaaccctat gatgccacgg ccacctacct tagggccaag taataataac aatgtagcca cttttggagc tggatctgtt
ggtaattcac aacaattgag accaaattta acccatagta tggcaagcat gccaccacag agaacatcaa acgtaatgat
cacatccaac acaactgcac caaactgggc ctctcaagaa ggaacaagca aacagcaaga agccctgacg tctgcaggag
tccgcttccc cacaggtaca cctgcagcct ataccccaaa tcagtcactg caacaggcag taggtagcca gcaattttcc
cagagggcag tggctcctcc taaccagtta acaccagcag tgcaaatgag acccatgaac caaatgagcc aaacactaaa
tgggcaaacc atgggtcccc tcaggggtct gaatctcaga cccaatcagc taagcacaca gattttgcct aatttgaatc
agtcaggaac agggttgaat cagtcgagga cgggcatcaa ccagccacca tccctgacgc ccagcaattt tccttcaccc
aaccaaagtt ccagggcttt tcaaggaact gaccacagca gtgacttagc ttttgacttc ctcagccaac aaaatgataa
catgggccct gccctaaaca gtgatgctga tttcattgat tctttattga agacagagcc tggtaatgat gactggatga aagacatcaa
tcttgatgaa atcttggggga acaattccta aagaagaaag ggaagacaat ttacaaactc caagcactaa aaggcagtat
attacagaaa ctctgtagag gctgaactgt tgatgttcag gtggactaca tgaagataac atgcttaaaa atggaaagca
gaaagtaact gcagtgatga acatttggt ccaaattctt gttttaaatc ttacacctga aagtaaaata ttgggatcac ttttccctgt
ctaaactcca ggatacagta tccaatttat ccaaacagaa ctgtggtgtc aatgtgtaat taattgtgta aaatagcctt cccaagtttc
tttccctg gaaaataaaa aaggtaatag aacttgtagt ttattttaaac cccatgtcat gaggaggtac tagttccaag caacaaactc
cttaatttgc tctaatagat aggtatggtt taatctttcc attgtgtctt ttcatttaat ttcctgaag cttgcaggat agattgaaat
gttataggtt tgtttggagt aaccaaacag tatgcaaatt aagaaaaagc cagagaacct agaaaacatc cagtggatta
cagaatttct tcccatatt cactcctcac ttttacaatt ttcccacaat cctctacttc agtgggatgc tgtgtctagt gattaaacaa
aaatatagag ctg

FIGURE 1

SEQ ID NO: 2

T TGG CAG GAG ATA GGT TAA CTA CCT GTT GAAGCTTGAGC AGG TGG TTA ATC TAT CTC CTG CTA ACA G TTTTTT

SEQ ID NO: 3

ATGTGCAGCGCGATCTTCTCGCTGAATGAAGCTTGATTCGGCGAGAAGGTCGCGTTG CACGATCAGTTTTTT

SEQ ID NO: 4

GATCAAAAAACTGATCGTGCAACGCGACCTTCTCGCCGAATCAAGCTTCATTCAGCG AGAAGATCGCGCTGCACAATCG

SEQ ID NO: 5

T TGG CAG GAG ATA GGT TAA CTA CCT GTT

SEQ ID NO: 6

A TTG TGC AGC GCG ATC TTC TCG CTG AAT

SEQ ID NO: 7

A TTC AGC GAG AAG ATC GCG CTG CAC AAC

SEQ ID NO: 8

CCUAUCUCCUGCCAACAGC

SEQ ID NO: 9

GGAUAGAGGACGGUUGUCG

SEQ ID NO: 10

CAGGUAGUUAACCUAUCUC

SEQ ID NO: 11

GUCCAUCAAUUGGAUAGAG

FIGURE 1 continued

SEQUENCE LISTING

```
<160> NUMBER OF SEQ ID NOS: 11

<210> SEQ ID NO 1
<211> LENGTH: 3763
<212> TYPE: DNA
<213> ORGANISM: Homo sapiens

<400> SEQUENCE: 1
aggtggcggc gagaagatgg cgacttcgaa caatccgcgg aaattcagcg agaagatcgc      60
gctgcacaat cagaagcagg cggaggagac ggcggccttc gaggaggtca tgaaggacct     120
gagcctgacg cgggccgcgc ggctccaggg ttccttgaaa agaaaacagg tagttaacct     180
atctcctgcc aacagcaagc gacccaatgg ctttgtggac aactcatttc ttgatatcaa     240
aagaattcgt gttggggaga atctctctgc aggacaaggt ggcctccaaa taaacaatgg     300
acaaagtcag attatgtcag ggaccttgcc tatgagccaa gcaccctgc  gaaagactaa     360 cactctgcca tcccatacac attctcctgg caatggcctg tttaacatgg gcttaaagga     420
ggtaaagaag gagccaggag agactctgtc ttgcagtaag cacatggatg gccaaatgac     480
```

-continued

```
ccaagagaat attttcccta ataggtacgg agacgaccct ggagaacaac tgatggatcc   540
tgagctgcag gaactgttca atgaactgac caacatatct gtgcctccca tgagtgacct   600
tgaactggaa acatgatcca atgccaccat aaagcaggat gacccattta acattgactt   660
gggtcagcaa agccagagga gcacacctag ccctccttta cccatggaga aaatagtgat   720
caaaagtgaa tactcaccgg gcttgactca ggggcccctca ggctctcctc agctgaggcc   780
cccatcagct ggccccgcat tctccatggc caactctgcc ctctccactt cgtctccaat   840
cccttcagtc cctcagagcc aggctcagcc tcagacaggc tccggagcaa gccgggcctt   900
gccaagctgg caggaagtat cccatgccca gcagctcaaa cagatagctg ctaatcgtca   960
gcagcatgcc cggatgcagc agcaccagca gcagcaccag cctaccaact ggtcagcctt  1020
gccctcctct gctggaccat caccaggtcc atttgggcag gagaaaatcc ccagcccttc  1080
ttttggtcag cagacattca gcccacagag ctcccccatg cctggggtag ctggcggcag  1140
cggccagtcg aaagtaatgg ctaactacat gtacaaggcc ggcccctcag cccagggtgg  1200
gcacctagat gtcctcatgc agcaaaagcc tcaggatctc agtcgaagtt ttattaacaa  1260
cccgcaccca gccatggagc cccgtcaggg caacaccaag cctttgtttc attttaactc  1320
agatcaagcg aaccagcaga tgccttctgt tttgccttcc cagaacaagc cttctctcct  1380
acactacacc caacagcaac agcagcaaca gcagcagcag cagcagcagc agcagcagca  1440
acagcagcag cagcagcaac agcaacagca acagcaacag cagagttcaa tttcagctca  1500
acaacagcaa cagcagcaga gctcaatttc agcccaacag cagcagcagc agcaacaaca  1560
gcagcagcag cagcaacaac aacagcaaca acagcagcag cagcagcagc aacaaccatc  1620
ttctcagcct gcccaatctc taccaagcca gcctttgcta aggtcacctt tgccacttca  1680
gcaaaagctc ctacttcagc aaatgcagaa tcagcccatt gcaggaatgg gataccaagt  1740
ctcccaacaa cagagacagg atcaacactc tgtggtaggc cagaacacag gccccagtcc  1800
aagtcctaac ccctgctcaa atccaaacac tggaagtggt tacatgaact cccagcaatc  1860
actgttgaat cagcaattga tgggaaagaa gcagactcta cagaggcaga tcatggagca  1920
gaaacagcaa cttcttctcc agcagcagat gctggctgac gcggagaaaa ttgctccaca  1980
agatcagata aaccgacatt tgtcaaggcc acctccagat tataaagacc aaagaagaaa  2040
tgtgggcaat atgcaaccaa ctgctcagta ttctggtggc tcatccacaa taagcttaaa  2100
ctctaaccag gctttggcaa acccagtttc aacacacacc attttaactc ccaattccag  2160
cctcctgtct acttctcacg ggacaagaat gccatcatta tctacagcag ttcagaatat  2220
ggggatgtat ggaaatctgc cttgtaatca acctaacaca tacagtgtca cttcaggaat  2280
gaatcaattg acccaacaga gaaacccaaa gcaattgtta gcaaatcaaa caaaccctat  2340
gatgccacgg ccacctacct tagggccaag taataataac aatgtagcca cttttggagc  2400
tggatctgtt ggtaattcac aacaattgag accaaattta acccatagta tggcaagcat  2460
gccaccacag agaacatcaa acgtaatgat cacatccaac acaactgcac caaactgggc  2520
ctctcaagaa ggaacaagca acagcaagca agccctgacg tctgcaggag tccgcttccc  2580
cacaggtaca cctgcagcct ataccccaaa tcagtcactg caacaggcag taggtagcca  2640 gcaatttttcc cagagggcag tggctcctcc taaccagtta acaccagcag tgcaaatgag  2700
acccatgaac caaatgagcc aaacactaaa tgggcaaacc atgggtcccc tcagggggtct  2760 gaatctcaga cccaatcagc taagcacaca gattttgcct aatttgaatc agtcaggaac  2820
```

-continued

```
agggttgaat cagtcgagga cgggcatcaa ccagccacca tccctgacgc ccagcaattt    2880
tccttcaccc aaccaaagtt ccagggcttt tcaaggaact gaccacagca gtgacttagc    2940
ttttgacttc ctcagccaac aaaatgataa catgggccct gccctaaaca gtgatgctga    3000
tttcattgat tctttattga agacagagcc tggtaatgat gactggatga aagacatcaa    3060
tcttgatgaa atcttgggga acaattccta aagaagaaag ggaagacaat ttacaaactc    3120
caagcactaa aaggcagtat attacagaaa ctctgtagag gctgaactgt tgatgttcag    3180
gtggactaca tgaagataac atgcttaaaa atggaaagca gaaagtaact gcagtgatga    3240
acattttggt ccaaattctt gttttaaatc ttacacctga agtaaaata ttgggatcac     3300 ttttccctgt ctaaactcca ggatacagta tccaatttat ccaaacagaa ctgtggtgtc    3360
aatgtgtaat taattgtgta aaatagcctt cccaagtttc tttttccctg gaaaataaaa    3420
aaggtaatag aacttgtagt ttatttaaac cccatgtcat gaggaggtac tagttccaag    3480
caacaaactc cttaatttgc tctaatagat aggtatggtt taatctttcc attgtgtctt    3540
ttcatttaat tttcctgaag cttgcaggat agattgaaat gttataggtt tgtttggagt    3600
aaccaaacag tatgcaaatt aagaaaaagc cagagaacct agaaaacatc cagtggatta    3660
cagaatttct tccccatatt cactcctcac ttttacaatt ttcccacaat cctctacttc    3720
agtgggatgc tgtgtctagt gattaaacaa aaatatagag ctg                       3763
```

```
<210> SEQ ID NO 2
<211> LENGTH: 73
<212> TYPE: DNA
<213> ORGANISM: Unknown
<220> FEATURE:
<223> OTHER INFORMATION: RNAi clone

<400> SEQUENCE: 2
ttggcaggag ataggttaac tacctgttga agcttgagca ggtggttaat ctatctcctg    60
ctaacagttt ttt                                                        73

<210> SEQ ID NO 3
<211> LENGTH: 71
<212> TYPE: DNA
<213> ORGANISM: Unknown
<220> FEATURE:
<223> OTHER INFORMATION: RNAi clone

<400> SEQUENCE: 3
atgtgcagcg cgatcttctc gctgaatgaa gcttgattcg gcgagaaggt cgcgttgcac    60
gatcagtttt t                                                          71

<210> SEQ ID NO 4
<211> LENGTH: 78
<212> TYPE: DNA
<213> ORGANISM: Unknown
<220> FEATURE:
<223> OTHER INFORMATION: RNAi clone - antisense

<400> SEQUENCE: 4
gatcaaaaaa ctgatcgtgc aacgcgacct tctgccgaat caagcttcat tcagcgagaa    60
gatcgcgctg cacaatcg                                                   78

<210> SEQ ID NO 5
<211> LENGTH: 28
<212> TYPE: DNA
<213> ORGANISM: Unknown
```

```
<220> FEATURE:
<223> OTHER INFORMATION: fragment of Mect1-MAML2 sequence

<400> SEQUENCE: 5
ttggcaggag ataggttaac tacctgtt                                              28

<210> SEQ ID NO 6
<211> LENGTH: 28
<212> TYPE: DNA
<213> ORGANISM: Unknown
<220> FEATURE:
<223> OTHER INFORMATION: fragment of Mect1-MAML2 sequence

<400> SEQUENCE: 6
attgtgcagc gcgatcttct cgctgaat                                              28

<210> SEQ ID NO 7
<211> LENGTH: 28
<212> TYPE: DNA
<213> ORGANISM: Unknown
<220> FEATURE:
<223> OTHER INFORMATION: fragment of Mect1-MAML2 sequence

<400> SEQUENCE: 7
attcagcgag aagatcgcgc tgcacaac                                              28

<210> SEQ ID NO 8
<211> LENGTH: 19
<212> TYPE: RNA
<213> ORGANISM: Unknown
<220> FEATURE:
<223> OTHER INFORMATION: siRNA #1

<400> SEQUENCE: 8
ccuaucuccu gccaacagc                                                        19

<210> SEQ ID NO 9
<211> LENGTH: 19
<212> TYPE: RNA
<213> ORGANISM: Unknown
<220> FEATURE:
<223> OTHER INFORMATION: complement to siRNA #1

<400> SEQUENCE: 9
ggauagagga cgguugucg                                                        19

<210> SEQ ID NO 10
<211> LENGTH: 19
<212> TYPE: RNA
<213> ORGANISM: Unknown
<220> FEATURE:
<223> OTHER INFORMATION: siRNA #2

<400> SEQUENCE: 10
cagguaguua accuaucuc                                                        19

<210> SEQ ID NO 11
<211> LENGTH: 19
<212> TYPE: RNA
<213> ORGANISM: Unknown
<220> FEATURE:
<223> OTHER INFORMATION: complement to siRNA #2

<400> SEQUENCE: 11
guccaucaau uggauagag                                                        19
```

COMPOSITIONS AND METHODS FOR INHIBITING TRANSLATION OF A MECT1-MAML2 CHIMERIC GENE

FIELD OF THE INVENTION

This invention pertains to compositions and methods for inhibiting the translation of a chimeric gene, such as the Mect1-MAML2 chimeric gene.

BACKGROUND OF THE INVENTION

The annual U.S. incidence rate of head and neck cancer is approximately 40,000 cases (Vokes et al., *New Eng. J. Med.*, 328: 184 (1993)). Although salivary gland tumors differ in their etiology, histology and standard therapy from most head and neck cancer, these cancers represent a significant threat to human health. Salivary gland tumors arise from either one of the three major salivary glands or from the minor salivary glands that line the mucosa of the upper aerodigestive tract. Histologically, these tumors are very heterogenous, and include mucoepidermoid cancers, pleomorphic adenoma, and adenoid cystic carcinomas as the more frequent observed tumor types. Treatment of these tumors is predominantly surgical, with post-operative radiotherapy being frequently administered. For unresectable tumors, neutron irradiation has been used in place of conventional radiotherapy. Chemotherapy is typically reserved for patients with recurrent or metastatic disease.

Mucoepidermoid carcinoma is the most common malignant human salivary gland tumor, which can arise from both major (parotid) and minor salivary glands, including serous/mucous glands within the pulmonary tracheobronchial tree (Calcaterra, in *Cancer Treatment*, 4th ed. (Haskell, ed.), W. B. Saunders Company, Philadelphia (1995), at pages 721-726). These salivary gland tumors can be deadly, due to their tendency to grow locally and recur aggressively, if not completely excised. However, complete excision is difficult due to the three-dimensional growth pattern of these tumors, which makes it difficult for the surgeon to determine accurately when clean margins have been achieved. Pathologic analysis using light microscopy is currently employed to assess tumor margins and to help determine the need for post-operative radiotherapy. However, this approach does not necessarily provide sufficient sensitivity for optimal patient management. In addition, both surgeons and patients desire minimal surgical approaches for cosmetic reasons, as well as to preserve nerve function to the facial area.

A chromosomal translocation has been implicated in certain forms of cancer. See, Tonon et al., "t(11;19)(q21;p13) translocation in mucoepidermoid carcinoma creates a novel fusion product that disrupts a Notch signaling pathway," *Nat. Genet.* (Advanced Online publication): 1-6 (2003). In particular, a t(11;19) translocation has been observed in some cancers of mucoepidermoid origin. In such cases, this may be the sole cytogenetic alteration. This chromosomal translocation has been noted to result in the expression of a chimeric gene, called Mect1-MAML2. Nucleotide sequencing identified the chimeric species as comprising exon 1 of the novel gene at 19p12-13 (Mect1) fused in-frame to exons 2-5 of MAML2. A further description of the Mect1-MAML2 fusion product is contained in commonly-owned, co-pending international patent application no. PCT/US02/021344, the disclosure of which is hereby incorporated in its entirety by reference. The sequence of Mect1-MAML2 has been fully elucidated, and its sequence is available from GenBank as Accession No. AY040324.1 (see also FIG. 1).

Full-length MAML2 appears to function as a CSL-dependent transcription co-activator for ligand-stimulated Notch, much like *Drosophila melanogaster* Mastermind and MAML1 factors. In particular, these Mastermind-like transcriptional co-activators form a complex in the nucleus with the intracellular domain of an activated Notch receptor (ICN) and the bifunctional transcription factor CSL.

Recently, a putative function for Mect1 was identified— Mect1 appears to be a member of a conserved family of co-activators that enhance CRE-dependent transcription via a phosphorylation-independent interaction with the bZIP DNA binding/dimerization domain of CREB. Mect1 recruitment does not appear to modulate CREB DNA binding activity, but rather enhances the interaction of CREB with the $TAF_{II}130$ component of TFIID following its recruitment to the promoter. CREB belongs to a group whose phosphorylation enhances their transactivation potential. The CREB transactivation domain is bipartite, consisting of kinase-inducible and constitutive activators that function cooperatively in response to cAMP agonist. For a further discussion of the function of Mect1 (also called TORC for Transducers of Regulated CREB activity), see Conkright et al., "TORCs: Transducers of Regulated CREB Activity," *Molecular Cell* 12: 413-423 (2003), and Iourgenko et al., "Identification of a family of cAMP response element-binding protein coactivators by genome-scale functional analysis in mammalian cells," *Proc. Natl. Acad. Sci.* (Early Edition, 2003).

Also recently reported are double-stranded RNA molecules for the inhibition of translation of particular gene products. RNAi is an evolutionarily conserved phenomenon and a multistep process that involves generation of active small interfering RNA in vivo through the action of an RNase III endonuclease, Dicer. The resulting short RNA molecules mediate degradation of the complementary homologous RNA. General description of RNAi compositions and methodology have been discussed in, e.g., Sui et al., "A DNA vector-based RNAi technology to suppress gene expression in mammalian cells," *Proc. Natl. Acad. Sci.* 99(8): 5515-5520 (2002), and U.S. Pat. No. 6,506,559 (Fire et al.), the disclosures of which are hereby incorporated in their entirety by reference.

A further technique, which also has been developed, is the use of siRNAs (small interfering RNA) to induce gene-specific suppression. The siRNAs are long enough to induce gene-specific suppression, but short enough to evade the host interferon response. The host interferon response is an antiviral defense mechanism that includes the production of interferon, resulting in non-specific degradation of RNA transcripts and a general shutdown of host cellular protein synthesis. See, Shi, "Mammalian RNAi for the masses," *TRENDS Genet.* 19(1): 9-12 (2003), incorporated herein in its entirety by reference.

The invention provides methods and compositions for inhibiting the translation of the Mect1-MAML2 chimeric gene. This and other objects and advantages, as well as additional inventive features, will be apparent from the description of the invention provided herein.

SUMMARY OF THE INVENTION

The present invention provides a composition for the inhibition of the translation of a Mect1-MAML2 chimeric gene consisting essentially of: (a) a fragment of the Mect1-MAML2 chimeric gene and (b) a nucleic acid complementary to the fragment. The fragment can be about 17 to about 32 nucleotides in length.

The present invention also provides a method of inhibiting the translation of a Mect1-MAML2 chimeric gene in a cell. The method comprises contacting the cell expressing the Mect1-MAML2 chimeric gene with a composition for the inhibition of the translation of a Mect1-MAML2 chimeric gene, whereupon the translation of the Mect1-MAML2 chimeric gene in the cell is inhibited.

BRIEF DESCRIPTION OF THE FIGURES

FIG. 1 sets forth the nucleotide sequences of SEQ ID NOS: 1-11, wherein the sequences are presented 5'-3' from upper left to lower right.

DETAILED DESCRIPTION

The present invention is drawn to compositions and methods for inhibiting the translation of particular sequences encoding a chimeric gene. In preferred embodiments, the chimeric gene is implicated in cancer. In highly preferred embodiments, the cancer is of mucoepidermoid origin. More highly preferred proteins of interest include a chimeric gene arising out of a chromosomal translocation. Ideally, the chromosomal translocation is a t(11; 19) translocation, such as the one giving rise to a Mect1-MAML2 chimeric gene. As such, in highly preferred embodiments, the present invention provides compositions and methods for inhibiting the translation of the Mect1-MAML2 chimeric gene.

In particular, the Mect1-MAML2 chimeric gene can have the DNA sequence of SEQ ID NO: 1. The amino acid sequence of the Mect1-MAML2 chimera is set forth as SEQ ID NO: 12. One of ordinary skill in the art will recognize that the Mect1-MAML2 chimeric gene can have other sequences, yet still give rise to the same protein, due to the degeneracy of the DNA code. Further one of ordinary skill in the art will recognize that many homologues of the Mect1-MAML2 chimeric gene will exist, such as those sharing about 99%, about 97%, about 95%, about 90%, about 85%, about 80%, about 75%, about 70%, about 60%, about 50%, about 25% or about 10% homology with the Mect1-MAML2 chimeric gene having the DNA sequence of SEQ ID NO: 1. As such, these sequences are also contemplated to be within the scope of those sequences that can be inhibited in accordance with the present invention.

One of ordinary skill in the art will also recognize that some sequences can be identified by their ability to hybridize to SEQ ID NO: 1 or its complement under highly stringent conditions. By "high stringency conditions," is meant conditions that distinguish a polynucleotide with an exact complementary sequence from one containing a only few small regions (e.g., 3-10 bases) with exact complementary sequence. Such small regions of complementarity are more easily melted than a full-length complement of 14-17 or more bases and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch. It is generally appreciated that conditions can be rendered more stringent by the addition of increasing amounts of formamide. Such sequences are also contemplated to be within the scope of the present invention, as being a target for inhibition by the present inventive compositions and methods.

Accordingly, the present invention provides a composition for the inhibition of the translation of a Mect1-MAML2 chimeric gene consisting essentially of, or consisting of: (a) a fragment of the Mect1-MAML2 chimeric gene, and (b) a nucleic acid complementary to the fragment. The fragment can be about 17 to about 32 nucleotides in length, such as about 17 to about 22 nucleotides, e.g., about 19 to about 21 nucleotides, or 21 to about 32 nucleotides in length, e.g., about 28 to about 29 nucleotides in length. The fragment can have the nucleotide sequence of SEQ ID NO: 5 or 6. In highly preferred embodiments of the present invention, the composition has the sequence of SEQ ID NO. 2, 3, or 4.

Alternatively, siRNA technology can be used to inhibit the translation of the Mect1-MAML2 chimeric gene. It is, therefore, preferred that the fragment is about 15, about 16, about 17, about 18, about 19, about 20, about 21, about 22, about 23, about 24, or about 25 nucleotides in length. More preferred is that the fragment is about 18 to about 22 nucleotides in length. Still more preferred is that the fragment is about 19 to about 21 nucleotides in length. In highly preferred embodiments, the fragment can have the nucleotides sequence of SEQ ID NO: 8 or 9.

The nucleic acid molecule complementary to the fragment can have from 1 to about 10 base substitutions, and may optionally contain one or more insertions. The nucleic acid complementary to the fragment can be about 19 to about 35 nucleotides in length. The Mect1-MAML2 chimeric gene can have the nucleotide sequence of SEQ ID NO: 1. The nucleic acid molecule complementary to the fragment can have from about 2 to about 5 substitutions. The nucleic acid molecule complementary to the fragment can have the sequence of SEQ ID NO: 7. The nucleic acid complementary to the fragment can optionally comprise some substitutions, deletions, insertions, and/or inversions. In some embodiments, it can be preferred to discuss the degree to which the sequence is complementary to the sequence of the fragment by the percent identity the fragment would share to the exact complementary sequence to the fragment. The sequence can share about 99%, about 97%, about 95%, about 90%, about 85%, about 80%, about 75%, about 70%, about 60%, about 50%, the chimeric gene, e.g., the sequence encoding Mect1-MAML2 chimeric gene, or, more preferably, SEQ ID NO: 1. Alternatively, the complementary sequence can be described with respect to the number of base substitutions contained in the complementary sequence as compared to the sequence of the short fragment of DNA. In preferred embodiments, the complementary sequence can contain about 1, about 2, about 3, about 4, about 5, about 6, about 7, about 8, about 9, about 10, or more substitutions. Preferably, the number of substitutions will be in the range of about 1 to about 10. More preferably, the number of substitutions will be in the range of about 1 to about 9. Still more preferably, the number of substitutions will be in the range of about 1 to about 8. Alternatively, the number of substitutions will be in the range of about 1 to about 7. The number of substitutions can also be in the range of about 1 to about 6. Ideally, the number of substitutions will be in the range of about 1 to 5.

In some preferred embodiments, the short fragment of a DNA sequence encoding a chimeric gene and its substantially complementary sequence can be linked by a linker sequence. Exemplary linkers include restriction endonuclease sequences. Such sequences are well-known in the art. Particularly preferred are endonuclease sequences that are at least about 4 nucleotides in length. Highly preferred are endonuclease sequences that are at least about 6 nucleotides in length. Of course, the endonuclease sequence can be longer than about 6 nucleotides in length. In some embodiments, the endonuclease sequence will be a Hin dIII restriction site (AAGCTT). One of ordinary skill in the art will recognize that the endonuclease sequence itself is not essential for the operability of the RNAi molecule. As such, the invention is not intended to be limited by any particular endonuclease disclosed herein.

The composition can be in a vector, which can be a plasmid or a viral vector, such as a adenoviral vector. Vectors include nucleic acid vectors, such as naked DNA and plasmids, and viral vectors, such as retroviral vectors, parvovirus-based vectors (e.g., adenoviral-based vectors and adeno-associated virus (AAV)-based vectors), lentiviral vectors (e.g., Herpes simplex (HSV)-based vectors), and hybrid or chimeric viral vectors, such as an adenoviral backbone with lentiviral components (see, e.g., Zheng et al., *Nat. Biotech.*, 18(2), 176-80 (2000); International Patent Application WO 98/22143; International Patent Application WO 98/46778; and International Patent Application WO 00/17376) and an adenoviral backbone with AAV components (see, e.g., Fisher et al., *Hum. Gene Ther.*, 7, 2079-2087 (1996)). Vectors and vector construction are known in the art (see, e.g., Sambrook et al., *Molecular Cloning: A Laboratory Manual*, 2d edition, Cold Spring Harbor Laboratory, NY (1989); and Ausubel et al., Current Protocols in Molecular Biology, Green Publishing Associates and John Wiley & Sons, New York, N.Y. (1994)).

The fragment and the nucleic acid complementary to the fragment can be operably linked to any suitable promoter and other regulatory sequences (e.g., transcription and translation initiation and termination codons, which are specific to the type of host) to control the expression of the nucleic acid sequence encoding the fusion molecule. The promoter can be a native or normative promoter. The selection of promoters, including various constitutive and regulatable promoters, is within the skill of an ordinary artisan. Examples of regulatable promoters include inducible, repressible, and tissue-specific promoters. Specific examples include viral promoters, such as adenoviral promoters and AAV promoters. Additionally, combining the nucleic acid described above with a promoter is within the skill in the art.

In the composition, the fragment and the nucleic acid complementary to the fragment can be under the control of different promoters. The promoters can be RNA polymerase promoters, particularly RNA polymerase III, such as when siRNA is employed. Exemplary RNA polymerase III promoters include U6 and H1, both of which are well-known in the art. One of ordinary skill in the art will be able to employ any other RNA polymerase III promoter, and the invention is not intended to be limited to the use of any specific RNA polymerase III promoter.

The fragment and the sequence complementary thereto, with their respective promoters can be on the same nucleic acid molecule, in tandem, or on different nucleic acid molecules. The two sequences can be contacted with a cell expressing the chimeric gene separately, in either order, or together.

The fragment and nucleic acid complementary to the fragment can be such that, upon annealing of the transcripts of the fragment and nucleic acid complementary to the fragment, the annealed transcripts of the composition have a 3' overhang of 1 to about 4 nucleotides, such as about 2 or about 3 nucleotides, on one or both ends of the annealed transcripts. One or more of the nucleotides can be uridine. The 3' overhang can consist of 2 uridine residues.

A variety of techniques used to synthesize the present inventive oligonucleotides are known in the art. See, for example, Sambrook et al., 1989, supra; and Lemaitre et al., *Proc. Natl. Acad. Sci. USA* 84: 648-652 (1987). The oligonucleotides can alternatively by synthesized commercially by companies, such as Eurogentec, Belgium.

The present invention also provides a method of inhibiting the translation of a Mect1-MAML2 chimeric gene in a cell. The method comprises, consists essentially of, or consists of contacting the cell expressing the Mect1-MAML2 chimeric gene with the above-described composition, whereupon the translation of the Mect1-MAML2 chimeric gene in the cell is inhibited. The cell can comprise, consist essentially of, or consist of a t(11;19) translocation, wherein the translocation results in a Mect1-MAML2 chimeric gene. The cell can be in a host, such as a mammal, particularly a human.

The cell can be a cancerous cell of mucoepidermoid origin, and the inhibition of the translation of the Mect1-MAML2 chimeric gene results in the inhibition of the cancerous cell. The cancerous cell can be in a gland, particularly the salivary gland.

Methods for inhibiting the translation of a nucleic acid sequence are known in the art. In one preferred method, a nucleic acid coding for a sequence in the antisense orientation to the nucleic acid sequence encoding a chimeric gene can inhibit the translation of the Mect1-MAML2 chimeric gene. In an alternative method a ribozyme can be used to inhibit the translation of the Mect1-MAML2 chimeric gene. A vector expressing an antisense molecule can, thus, be designed translation of the chimeric gene. The antisense molecule preferably is at least about 20 nucleotides in length. The nucleic acid sequence introduced in antisense suppression generally is substantially identical to at least a portion, preferably at least about 20 contiguous nucleotides, of the gene to be targeted, but such that the inhibitory effect applies to other proteins within a family of genes exhibiting homology or substantial homology to the target gene. The introduced sequence also need not be full-length relative to either of the primary transcription product or fully processed mRNA. Generally, higher homology can be used to compensate for the use of a shorter sequence. Furthermore, the introduced sequence need not have the same intron or exon pattern, and homology of non-coding segments are equally effective. As an alternative to antisense suppression, interfering RNA can be used to achieve the same effect by a different mechanism of action.

Ribozymes can be designed such that they specifically pair with virtually any target RNA and cleave the phosphodiester backbone at a specific location, thereby functionally inactivating the target RNA. In carrying out this cleavage, the ribozyme is not itself altered and is, thus, capable of recycling and cleaving other molecules, making it a true enzyme. The inclusion of ribozyme sequences with antisense RNAs confers RNA-cleaving activity upon them, thereby increasing the activity of the constructs. The design and use of target RNA-specific ribozymes is described in Haseloff et al., *Nature* 334: 585-591 (1988). Preferably, the ribozyme comprises at least about 20 contiguous nucleotides complementary to the target sequence on each side of the active site of the ribozyme.

Alternatively, and more preferably, a nucleic acid molecule encoding an RNAi molecule can be used to inhibit the translation of a nucleic acid molecule encoding a chimeric gene. Such methods have been described, for example in Sui et al., "A DNA vector-based RNAi technology to suppress gene expression in mammalian cells," *Proc. Natl. Acad. Sci.* 99(8): 5515-5520 (2002), and U.S. Pat. No. 6,506,559 (Fire et al.). Other methods for inhibiting the translation of a nucleic acid sequence encoding a chimeric gene are also contemplated to be within the scope of the invention.

In highly preferred embodiments, RNAi technology is employed to inhibit the translation of a chimeric gene, such as the Mect1-MAML2 chimeric gene. RNAi technology contemplates short fragments of a nucleic acid sequence encoding a chimeric gene. As such, in preferred embodiments, the present invention contemplates the use of short fragments of a nucleic acid molecule encoding Mect1-MAML2 chimeric gene. Accordingly, in highly preferred embodiments, a short fragment of the sequence of SEQ ID NO: 1 can be used, together with a sequence substantially complementary to the fragment. By "short fragment" is meant a fragment that is about 5, about 10, about 15, about 17, about 18, about 19, about 20, about 21, about 22, about 23, about 24, about 25, about 26, about 27, about 28, about 29, about 30, about 31, about 32, about 34, about 36, about 38, about 40, about 45, or about 50 contiguous nucleotides in length.

The nucleic acid sequence of SEQ ID NO: 2 or 3 can be the RNAi molecule. SEQ ID NO: 2 has a fragment of the Mect1-MAML2 chimeric gene as described above. The fragment is followed by a Hin dIII restriction site, following the teachings of the present specification. Finally, the nucleic acid sequence complementary to the fragment follows which consists of about 1 to about 10 base substitutions and optionally one or more insertions. Furthermore, SEQ ID NO: 3 has been similarly constructed, together with its antisense strand, set forth as SEQ ID NO: 4. Accordingly, one of ordinary skill in the art, by following the teachings of the present specification, can construct many such RNAi molecules to inhibit the translation of a chimeric gene.

The present invention also provides methods, which utilize the compositions provided, supra. The present invention contemplates methods of inhibiting the translation of a chimeric gene. In preferred embodiments, the methods comprise the use of the technologies, as described above, to administer a nucleic acid molecule that inhibits the translation of the Mect1-MAML2 chimeric gene. In highly preferred embodiments, the methods comprise the administration of the RNAi molecules described, supra, to inhibit the translation of the Mect1-MAML2 chimeric gene. However, one of ordinary skill in the art should appreciate that any other method for inhibiting the translation of a chimeric gene that is known in the art, or that is developed in the art, is contemplated as being within the scope of the present invention. As such, methods including, but not limited to, technologies such as RNAi and antisense technology are contemplated as being within the scope of the invention.

These methods can be used with any organism that expresses a chimeric gene. Preferably, the organism is eukaryotic. More preferably, the organism is an animal, such as a mammal. For purposes of the present invention, mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

An organism can be in need of inhibition of the translation of a chimeric gene due to a condition arising out of abnormal cellular proliferation. The abnormal cellular proliferation can be cancer. The cancer can be of mucoepidermoid origin. The cancer of mucoepidermoid origin can result from a chromosomal translocation, such as a t(11;19) translocation. The t(11;19) translocation can give rise to a Mect1-MAML2 chimeric gene. The Mect1-MAML2 chimeric gene can have a nucleic acid sequence such as that described in SEQ ID NO: 1, or a sequence substantially identical thereto.

As such, RNAi technology can be employed to inhibit the translation of a Mect1-MAML2 chimeric gene. Such therapy can be useful for an organism in need of such inhibition of translation. In particular, an organism can have cancer of mucoepidermoid origin and/or can have a t(11;19) translocation. In particular exemplary embodiments, the organism can be administered the nucleic acid sequence of SEQ ID NO: 2 or the nucleic acid sequence of SEQ ID NO: 3 by any means known in the art to inhibit the translation of the Mect1-MAML2 chimeric gene. It is also contemplated that more than one RNAi sequence can be administered to an organism in need thereof, directed to the same chimeric gene, or to another chimeric gene. As such, combination therapy is contemplated, where multiple proteins of interest are implicated. A second translation-inhibitory molecule for a second chimeric gene, which may be administered concurrently, or sequentially (either before or after) the administration of the first translation-inhibitory molecule can be prepared in accordance with the teachings provided herein and known in the art.

The compositions and methods can be used in combination with other known treatment methods, such as radiation, surgery, or the administration of other active agents, such as adjuvants or other anti-cancer agents and their prodrugs. Such additional agents can be administered concurrently with or sequentially to, in either order, the compositions of the present invention. Examples of cytotoxic agents and their prodrugs include genistein, okadaic acid, 1-β-D-arabinofuranosyl-cytosine, arabinofuranosyl-5-aza-cytosine, cisplatin, carboplatin, actinomycin D, asparaginase, bis-chloro-ethyl-nitroso-urea, bleomycin, chlorambucil, cyclohexyl-chloro-ethyl-nitroso-urea, cytosine arabinoside, daunomycin, etoposide, hydroxyurea, melphalan, mercaptopurine, mitomycin C, nitrogen mustard, procarbazine, teniposide, thioguanine, thiotepa, vincristine, 5-fluorouracil, 5-fluorocytosine, adriamycin, cyclophosphamide, methotrexate, vinblastine, doxorubicin, leucovorin, taxol, anti-estrogen agents such as tamoxifen, intracellular antibodies against oncogenes, the flavonol quercetin, Guan-mu-tong extract, retinoids such as fenretinide, nontoxid retinoid analogues such as N-(4-hydroxyphenyl)-retinamide (HPR), and monoterpenes such as limonene, perillyl alcohol and sobrerol.

The present inventive compositions and methods can be used as a prophylaxis to a condition due to the translation of a chimeric gene. In such cases, it can be beneficial to inhibit the translation of the chimeric gene before a condition becomes evident, and becomes debilitating, or more difficult to treat therapeutically. As used in the context of the present invention, prophylaxis does not necessarily mean absolute prevention. One of ordinary skill in the art will appreciate that any degree of the inhibition of translation of a chimeric gene can be beneficial. As used herein, a prophylactic regimen can be administered upon the detection of the translation of a chimeric gene, whereby the effects of the translation of the chimeric gene are decreased when compared to the inventive compositions or methods are not given to the organism.

In accordance with the present invention, a patient suspected of having a cancer of mucoepidermoid origin can be tested to identify a chimeric gene. In particular, the chimeric gene can arise from a t(11;19) translocation. Such a chimeric gene can be a Mect1-MAML2 chimeric gene.

Suitable methods of determining whether or not a cell expresses a particular protein are known in the art (see, for instance, Sambrook et al., *Molecular Cloning: A Laboratory*

*Manual*, 2nd Ed., Cold Spring Harbor, N.Y., 1989). With regards to the present inventive methods, whether or not a cell expresses a chimeric gene, such as Mect1-MAML2, can be determined by, for example, Fluorescence-Activated Cell Sorting (FACS) using fluorescein isothiocyante (FITC)-conjugated antibodies, which recognize the chimeric gene, e.g., Mect1-MAML2. Western blotting or immunofluorescence also can be performed to determine whether or not a cell expresses the chimeric gene, e.g., Mect1-MAML2. These methods are well-known in the art. Other methods are provided in commonly owned, co-pending international application no. PCT/US02/021344, the disclosure of which is hereby incorporated in its entirety by reference.

The nucleic acid molecules and vectors can be administered to a mammal alone, or in combination with a pharmaceutically acceptable carrier. By pharmaceutically acceptable is meant a material that is not biologically or otherwise undesirable (i.e., the material can be administered to a mammal, along with the nucleic acid or vector without causing any undesirable biological effects or interacting in a deleterious manner with any of the other components of the pharmaceutical composition in which it is contained). The carrier is selected to minimize any degradation of the agent and to minimize any adverse side effects in the mammal, as would be well-known to one of ordinary skill in the art.

Suitable carriers and their formulations are described in Remington: The Science and Practice of Pharmacy (19th ed.) ed. A. R. Gennaro, Mack Publishing Company, Easton, Pa. (1995). Pharmaceutical carriers, include sterile water, saline, Ringer's solution, dextrose solution, and buffered solutions at physiological pH. Typically, an appropriate amount of a pharmaceutically acceptable salt is used in the formulation to render the formulation isotonic. The pH of the solution is preferably from about 5 to about 8 (e.g., about 5.5, about 6, about 6.5, about 7, about 7.5, and ranges thereof). More preferably, the pH is about 7 to about 7.5. Further carriers include sustained-release preparations, such as semipermeable matrices of solid hydrophobic polymers containing the fusion molecule, which matrices are in the form of shaped articles (e.g., films, liposomes, or microparticles). It will be apparent to those persons skilled in the art that certain carriers may be more preferable depending upon, for instance, the route of administration and concentration of composition being administered.

Compositions (e.g., pharmaceutical compositions) comprising the nucleic acid molecule or vector can include carriers, thickeners, diluents, buffers, preservatives, surface active agents and the like. The compositions can also include one or more active ingredients, such as antimicrobial agents, anti-inflammatory agents, anesthetics, and the like.

The composition (e.g., pharmaceutical composition) comprising the nucleic acid molecule or vector can be administered in any suitable manner, depending on whether local or systemic treatment is desired, and on the area to be treated. Administration can be topically (including ophthalmically, vaginally, rectally, intranasally, transdermally, and the like), orally, by inhalation, or parenterally (including by intravenous drip or subcutaneous, intracavity, intraperitoneal, or intramuscular injection). Topical intranasal administration refers to the delivery of the compositions into the nose and nasal passages through one or both of the nares and can comprise delivery by a spraying mechanism or droplet mechanism, or through aerosolization of the nucleic acid or vector. Administration of the compositions by inhalent can be through the nose or mouth via delivery by a spraying or droplet mechanism. Delivery can also be directly to any area of the respiratory system (e.g., lungs) via intubation.

If the composition is to be administered parenterally, the administration is generally by injection. Injectables can be prepared in conventional forms, either as liquid solutions or suspensions, solid forms suitable for solution of suspension in liquid prior to injection, or as emulsions. Additionally, parental administration can involve the preparation of a slow-release or sustained-release system, such that a constant dosage is maintained (see, e.g., U.S. Pat. No. 3,610,795). Preparations for parenteral administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases and the like.

Formulations for topical administration may include ointments, lotions, creams, gels, drops, suppositories, sprays, liquids, and powders. Conventional pharmaceutical carriers; aqueous, powder, or oily bases; thickeners; and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable.

Some of the compositions can potentially be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines.

The nucleic acid molecule or vector can be administered with a pharmaceutically acceptable carrier and can be delivered to the mammal's cells in vivo and/or ex vivo by a variety of mechanisms well-known in the art (e.g., uptake of naked DNA, liposome fusion, intramuscular injection of DNA via a gene gun, endocytosis, and the like).

Additionally, probiotic therapies are envisioned by the present invention. Viable host cells containing the nucleic acid or vector of the invention and expressing the fusion molecule can be used directly as the delivery vehicle for the fusion molecule to the desired site(s) in vivo. Preferred host cells for the delivery of the fusion molecule directly to desired site(s), such as, for example, to a selected body cavity, can comprise bacteria. More specifically, such host cells can comprise suitably engineered strain(s) of lactobacilli, enterococci, or other common bacteria, such as *E. coli*, normal strains of which are known to commonly populate body cavities. More specifically yet, such host cells can comprise one or more selected nonpathogenic strains of lactobacilli, such as those described by Andreu et al. (*J. Infect. Dis.*, 171(5), 1237-43 (1995)), especially those having high adherence properties to epithelial cells (e.g., vaginal epithelial cells) and suitably transformed using the nucleic acid or vector of the invention.

If ex vivo methods are employed, cells or tissues can be removed and maintained outside the body according to standard protocols known in the art. The compositions can be introduced into the cells via any gene transfer mechanism, such as calcium phosphate mediated gene delivery, electroporation, microinjection, or proteoliposomes. The transduced cells then can be infused (e.g., with a pharmaceutically acceptable carrier) or homotopically transplanted back into the mammal per standard methods for the cell or tissue type. Standard methods are known for transplantation or infusion of various cells into a mammal.

The exact amount of the compositions required to treat a viral infection will vary from mammal to mammal, depending on the species, age, gender, weight, and general condition of the mammal, the nature of the virus, the existence and extent of viral infection, the particular fusion molecule, nucleic acid, vector, or cell used, the route of administration, and whether other drugs are included in the regimen. Thus, it is not possible to specify an exact amount for every composition. However, an appropriate amount can be determined by one of ordinary skill in the art using only routine experimentation given the teachings herein. Effective dosages and schedules for administering the nucleic acid molecules, vectors, cells, and fusion molecules of the invention can be determined empirically, and making such determinations is within the skill in the art. The dosage ranges for the administration of the compositions are those large enough to produce the desired effect; however, the dosage should not be so large as to cause adverse side effects, such as unwanted cross-reactions, anaphylactic reactions, and the like. Dosage can vary, and can be administered in one or more (e.g., two or more, three or more, four or more, or five or more) doses daily, for one or more days. The composition can be administered before viral infection or immediately upon determination of viral infection and continuously administered until the virus is undetectable.

As used herein, the term "inhibits," and words stemming therefrom, do not necessarily imply 100% or complete inhibition. Rather, there are varying degrees of inhibition of which one of ordinary skill in the art recognizes as having a potential benefit or therapeutic effect. In this regard, the translation-inhibitory nucleic acid molecule of the present invention can achieve any level of inhibition of translation of a chimeric gene. Desirably, if the contacted cell is a cancerous cell, such as a cancerous cell in a host, the translation-inhibitory molecule inhibits at least 10% of the tumor cell metastasis or growth, which occurs in the absence of any composition or method described herein. It is more preferred that the translation inhibitory molecule achieves at least a 50% inhibition. Most preferred is that translation inhibitory molecule inhibits at least about 90%, about 95%, about 97% or even greater of the tumor cell metastasis or tumor cell growth than that which occurs in the absence of treatment.

EXAMPLES

The following examples serve to illustrate the present invention and are not intended to limit its scope in any way.

Example 1

This example demonstrates the construction of an RNAi translation-inhibitory molecule directed to a Mect1-MAML2 chimeric gene. A 29-nucleotide fragment (having the sequence of SEQ ID NO: 5) of the Mect1-MAML2 fusion gene was identified. The 29 base-pair fragment was followed by an artificial Hin dIII restriction site (AAGCTT) and then by a near-perfect complement (as provided by the specification) to the 29 nucleotides. The complete sequence of the composition is defined by SEQ ID NO: 2, and was designated as clone #4. The complete nucleic acid molecule (having SEQ ID NO: 2) was obtained by oligonucleotide synthesis from Sigma-Genosys (The Woodlands, Tex.).

This clone was subcloned into the pSHAG plasmid, under control of a U6 promoter. The pSHAG plasmid also includes a neomycin resistance selectable marker. Control plasmids contained a firefly RNAi molecule (FF), which is not specific for Mect1-MAML2, or mt4 (one base difference from the sequence of clone #4). These were transfected into H292 cells, which contain the t(11;19) translocation. A mock transfection (i.e., no vector given to the cells) was performed and the H292 cells were exposed to neomycin. Absence of the growth of cells demonstrated sensitivity of the H292 cells to neomycin. The plasmids containing #4, mt4 or FF or vector containing no transgene were transfected into the H292 cells using lipofectamine reagent (available from Clontech, Palo Alto, Calif.).

The plasmid containing #4 effectively inhibited the growth of tumor cells. Cells transfected with the vector alone were able to grow, as the vector conferred resistance to neomycin to the H292 cells. The control plasmid did not inhibit the growth of tumor cells, whereas those cells transfected with #4 were dramatically inhibited. The control demonstrates that the marked inhibition is not a result of the presence of some exogenous RNA resulting from the expression of the transgene. As such, the RNAi molecule specifically inhibited the growth of a tumor cell line expressing Mect1-MAML2. A single base difference in the fragment section of the RNAi molecule, such as in mt4, is sufficient to decrease the inhibition of the cancer cells.

A similar experiment was performed on HSY cells (salivary gland tumor lines that do not have a t(11;19) translocation). These cells were transfected with #4 or vector containing no transgene. No inhibition of cancer cells was observed with #4 or the vector containing no transgene, although #4 was previously shown to inhibit the growth of cancerous cells with the t(11;19) translocation. As such, it is further confirmed that #4 specifically inhibits cells with a t(11;19) translocation, which translocation results in the Mect1-MAML2 chimeric gene.

This example demonstrates that an RNAi translation-inhibitory molecule directed to a Mect1-MAML2 chimeric gene can specifically inhibit cancer cells expressing a t(11;19) translocation.

Example 2

This example demonstrates that the RNAi translation inhibitory molecule can inhibit the translation of Mect1-MAML2. A lung tumor cell line (H2009) that does not express Mect1-MAML2 chimeric gene was transiently transfected with a vector to express Mect1-MAML2 (SEQ ID NO: 1). These cells were co-transfected with one of plasmid control (pSHAG), FF, #4, or mt4. Mect1-MAML2 was visualized on a polyacrylamide gel by protein immunoblot from cell extracts harvested at 3 days. The immunoblot demonstrates that #4 dramatically decreased the translation of Mect1-MAML2 relative to the controls, and mt4. This Example demonstrated that RNAi translation inhibitory molecules provided by the present invention are effective at specifically inhibiting the translation of the Mect1-MAML2 chimeric gene.

Example 3

This example demonstrates that siRNA sequences can inhibit the translation of a chimeric gene. Cells from the H2009 lung tumor cell line were transiently transfected with Mect1-MAML2 chimeric gene. Duplex synthetic RNA #1 (SEQ ID NOS: 8 and 9) or RNA #2 (SEQ ID NOS: 10 and 11) was transfected into cells using the pSHAG plasmid, as described, supra. The duplex sequence was obtained from Qiagen (Valencia, Calif.). A protein immunoblot of the transfected cells demonstrated a marked inhibition of the expression of Mect1-MAML2 protein relative to controls, which did not receive the siRNA treatment. This example demonstrated the ability of siRNA to inhibit the translation of Mect1-MAML2.

Example 4

This example demonstrates a vector to deliver a composition to cancer cells and thereby inhibit their growth. RNAi clone #4 from the preceding examples was ligated into a commercially available adenoviral vector (Ad-RNAi#4). H3118 tumor cells were contacted with crude viral lysates at MOI 90. Ad-RNAi#4 was able to inhibit dramatically cancer cells relative to control adenovirus that did not contain RNAi#4. This example demonstrates that a viral vector expressing an RNAi molecule can inhibit the translation of Mect1-MAML2, thereby inhibiting the growth of cancerous cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The phrase "consisting essentially of" where used herein, is intended to only limit the scope of the invention to the specified materials or steps, and those that do not materially affect the basic and novel characteristics of the claimed invention as set forth above. As such, the scope of the invention where "consisting essentially of" is recited is intended to be narrower than where "comprising" is used, however broader than where "consisting of" is used. One of skill in the art, in reviewing the present specification, can readily identify those materials and steps that do not materially affect the basic and novel characteristics of the present invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A composition for the inhibition of the translation of a Mect1-MAML2 chimeric gene, consisting essentially of: (a) a fragment of a nucleic acid encoding SEQ ID NO: 12 and (b) a nucleic acid complementary to the fragment, optionally comprising 1 to 3 substitutions, wherein the fragment of a nucleic acid encoding SEQ ID NO: 12 comprises the nucleotide sequence of SEQ ID NO: 5 or 6.

2. The composition of claim 1, wherein the fragment of a nucleic acid encoding SEQ ID NO: 12, the nucleic acid complementary to the fragment, or both are in a vector.

3. The composition of claim 2, wherein the vector is a plasmid.

4. The composition of claim 2, wherein the vector is a viral vector.

5. The composition of claim 4, wherein the viral vector is an adenoviral vector.

6. A composition for the inhibition of the translation of a Mect1-MAML2 chimeric gene, consisting essentially of nucleic acid comprising the nucleotide sequence of SEQ ID NO: 2, 3, or 4.

7. The composition of claim 1, wherein the fragment of a nucleic acid encoding SEQ ID NO: 12 and the nucleic acid complementary to the fragment are under the control of different promoters on the same nucleic acid molecule.

8. The composition of claim 7, wherein the promoters are RNA polymerase promoters.

9. The composition of claim 8, wherein the promoters are RNA polymerase III promoters.

10. A method of inhibiting the translation of a Mect1-MAML2 chimeric gene in a cell comprising contacting the cell expressing the Mect1-MAML2 chimeric gene with the composition of claim 1, whereupon the translation of the Mect1-MAML2 chimeric gene in the cell is inhibited.

11. The method of claim 10, wherein the cell comprises a t(11;19) translocation, wherein the translocation results in a Mect1-MAML2 chimeric gene.

12. The method of claim 10, wherein the cell is in a host.

13. The method of claim 12, wherein the host is a mammal.

14. The method of claim 13, wherein the mammal is a human.

15. The method of claim 13, wherein the cell is a cancerous cell of mucepidermoid origin and the inhibition of the translation of the Mect1-MAML2 chimeric gene results in the inhibition of the cancerous cell.

16. The method of claim 15, wherein the cancerous cell is in a gland.

17. The method of claim 16, wherein the gland is a salivary gland.

18. A method of inhibiting the translation of a Mect1-MAML2 chimeric gene in a cell comprising contacting the cell expressing the Mect1-MAML2 chimeric gene with the composition of claim 6, whereupon the translation of the Mect1-MAML2 chimeric gene in the cell is inhibited.

19. The method of claim 18, wherein the cell comprises a t(11;19) translocation, wherein the translocation results in a Mect1-MAML2 chimeric gene.

20. The method of claim 18, wherein the cell is in a host.

21. The method of claim 20, wherein the host is a mammal.

22. The method of claim 21, wherein the mammal is a human.

23. The method of claim 18, wherein the cell is a cancerous cell of mucepidermoid origin and the inhibition of the translation of the Mect1-MAML2 chimeric gene results in the inhibition of the cancerous cell.

24. The method of claim 23, wherein the cancerous cell is in a gland.

25. The method of claim 24, wherein the gland is a salivary gland.

26. The composition of claim 6, wherein the nucleic acid is in a vector.

27. The composition of claim 26, wherein the vector is a plasmid.

28. The composition of claim 26, wherein the vector is a viral vector.

29. The composition of claim 28, wherein the viral vector is an adenoviral vector.

30. An in vitro method of inhibiting the translation of a Mect1-MAML2 chimeric gene in a cell comprising contacting the cell expressing the Mect1-MAML2 chimeric gene with the composition of claim 1, whereupon the translation of the Mect1-MAML2 chimeric gene in the cell is inhibited.

31. An in vitro method of inhibiting the translation of a Mect1-MAML2 chimeric gene in a cell comprising contacting the cell expressing the Mect1-MAML2 chimeric gene with the composition of claim 6, whereupon the translation of the Mect1-MAML2 chimeric gene in the cell is inhibited.

* * * * *